United States Patent [19]

Kopf-Sill et al.

[11] Patent Number: 5,160,702
[45] Date of Patent: Nov. 3, 1992

[54] ANALYZER WITH IMPROVED ROTOR STRUCTURE

[75] Inventors: Anne R. Kopf-Sill, Portola Valley; Robert Zuk, Burlingame, both of Calif.

[73] Assignee: Molecular Devices Corporation, Menlo Park, Calif.

[21] Appl. No.: 297,563

[22] Filed: Jan. 17, 1989

[51] Int. Cl.⁵ .......................... G01N 9/30; B04B 11/00
[52] U.S. Cl. ...................................... 422/72; 422/100; 436/45; 494/17; 494/31
[58] Field of Search .................... 422/72, 100; 436/45; 494/16, 17, 18, 21, 31

[56] References Cited

U.S. PATENT DOCUMENTS

| | | | |
|---|---|---|---|
| 3,744,975 | 7/1973 | Mailen | 422/72 |
| 3,899,296 | 8/1975 | Mailen et al. | 422/72 |
| 3,901,658 | 8/1975 | Burtis et al. | 494/16 |
| 4,284,602 | 8/1981 | Kelton et al. | 422/72 |
| 4,431,606 | 2/1984 | Revillet et al. | 422/102 |
| 4,469,793 | 9/1984 | Guigan | 422/72 |
| 4,743,558 | 10/1985 | Guigan | 422/72 |
| 4,883,763 | 11/1989 | Holen et al. | 422/72 |
| 4,892,708 | 1/1990 | Wogoman | 422/72 |
| 4,999,304 | 3/1991 | Robertson | 422/72 |

Primary Examiner—Robert J. Warden
Assistant Examiner—T. A. Trembley
Attorney, Agent, or Firm—Allegretti & Witcoff, Ltd.

[57] ABSTRACT

An analyzer with an improved rotor structure for analyzing solid-containing and solid free liquids having an improved rotor design that utilizes chambers and channels that operate by centrifugal force and capillary action to separate and meter the liquids for testing purposes.

26 Claims, 5 Drawing Sheets

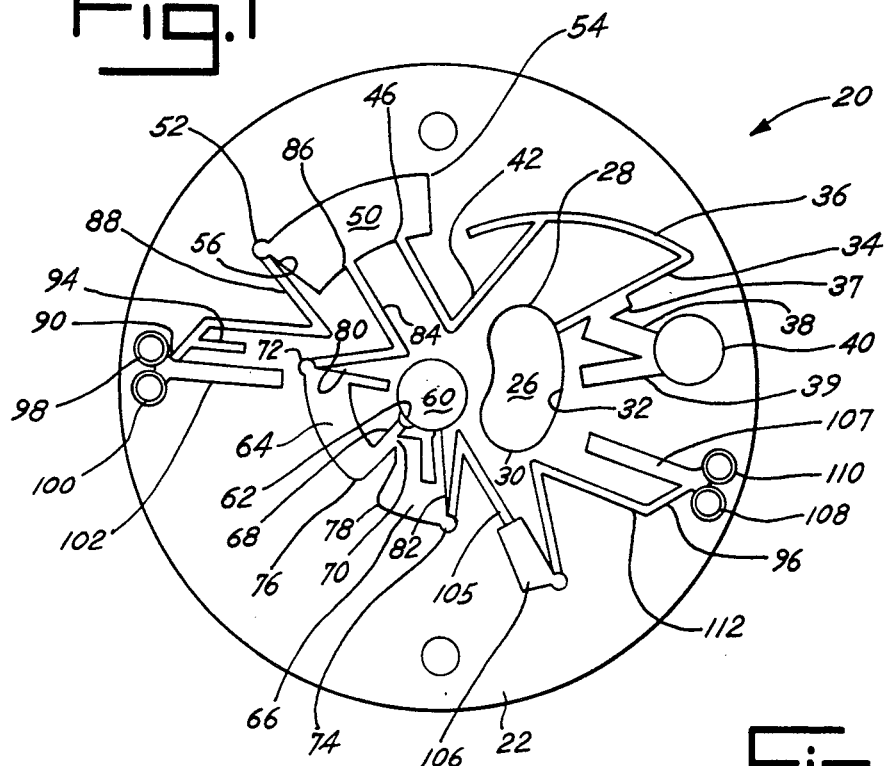
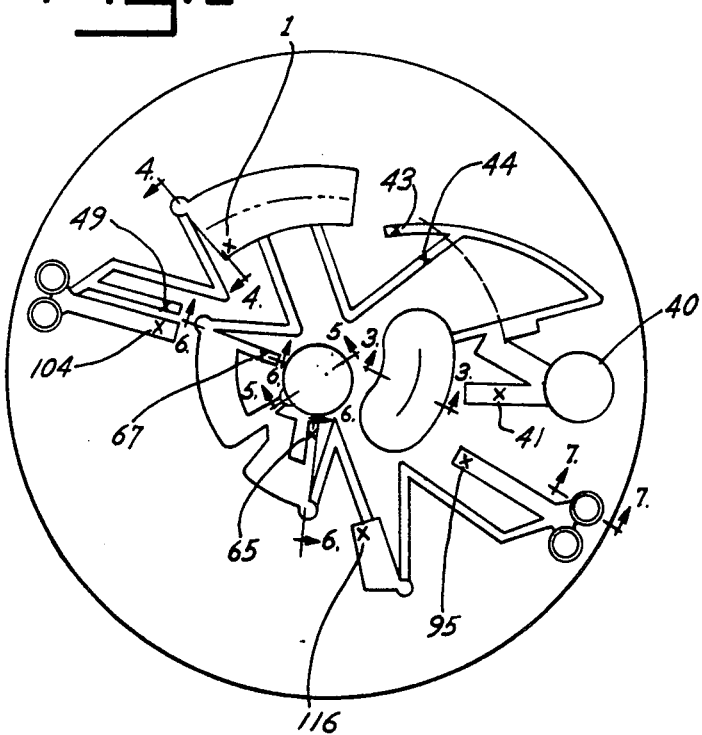
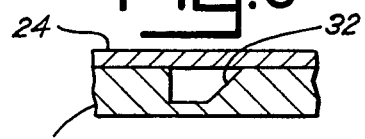
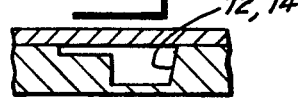
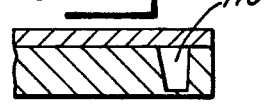

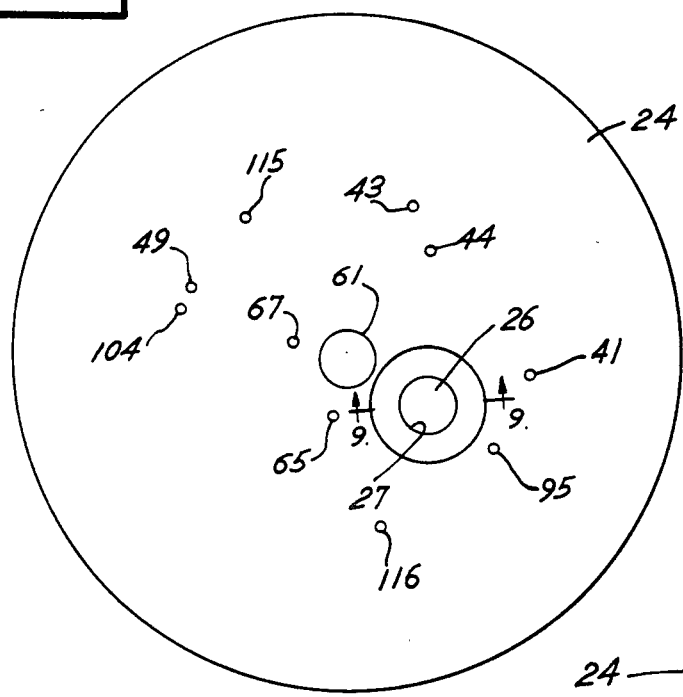
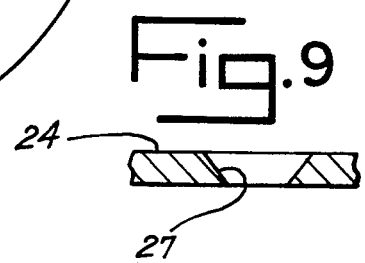
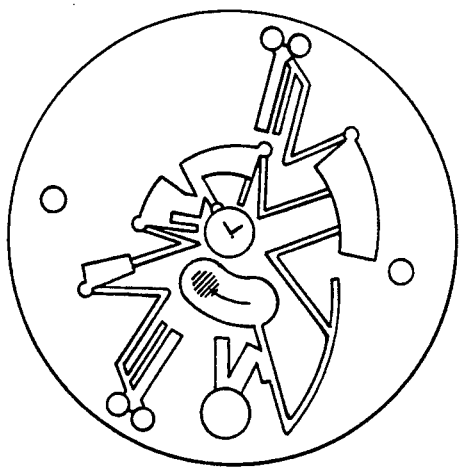
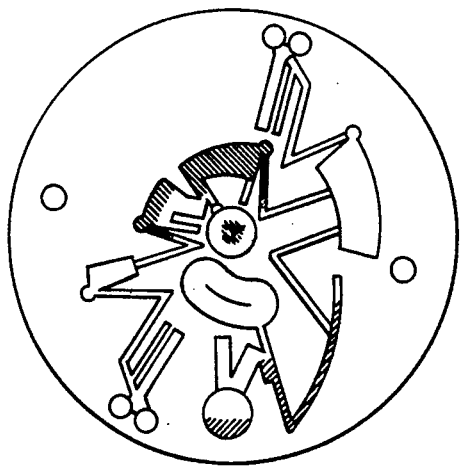

ANALYZER WITH IMPROVED ROTOR STRUCTURE

This invention relates to a centrifugal analyzer for solid-containing fluids and non-solid containing fluids with an improved rotor design. More particularly, it relates to a rotor for an analyzer which uses capillary action and centrifugal force to move, mix and meter fluids, separate a dense phase from a less dense phase or dissolve reagents.

PRIOR ART

U.S. Pat. No. 3,744,975 describes a rotor for a photometric analyzer for use in space where gravity does not function. The rotor comprises a central disc sandwiched between outer transparent plastic discs, said central disc having a circular array of axially extending apertures which serve as sample cuvettes. The cuvettes communicate through radial passageways to a central sample distribution chamber. These passageways connect to overflow cavities through capillary channels which prevent loss of sample when the rotor is not spinning. Additional passageways of V shape connect the ends of the radial passageways to the cuvettes and serve to trap particulates in the sample liquid. The underside of the rotor has a reagent distribution chamber which connects to the cuvettes through capillary passageways which retain liquid when the rotor is not spinning. Red cells are separated from the plasma and trapped in the outer ends of the radial passageways. Air pressure is required to force the plasma into the cuvettes. The rotor does not have means for automatically measuring the fluids so they have to be measured before introducing them into the rotor. It is disadvantageous to require a source of compressed air for moving the fluids through the passageways; or to have to introduce the reagent through the bottom of the rotor. Manual measurement prior to putting fluids into the rotor introduces human error.

U.S. Pat. No. 4,431,606 discloses an analytical rotor having analytical cells at the rotor periphery connecting to a central distribution chamber for reagent. The device contains no means for separating the sample. Thus, the separating step must be performed separately which requires extra time, equipment and in case of blood, adds extra contact with a potentially dangerous substance. As the rotor turns at slow speed, the reagent flows from the central chamber into a portioning cavity having the desired volume for accurate analysis. The cavity communicates with an overflow reservoir which insures filling of the cavity. A capillary passage connects the portioning cavity to the cuvette. Flow through the capillary is effected only at high rotor speeds. The cuvettes are not vented. Thus, the centrifugal force must be great enough to break the meniscus and allow the air to escape backwards through the capillary so that the reagent can enter the cuvettes. High speeds increase the cost of the machine and make it less safe. The amount of sample to be tested is measured by a pipette, independently of the rotor structure. This procedure is subject to error.

U.S. Pat. No. 4,284,602 discloses a similar device in which vented measuring chambers and connecting passageways are positioned between the central fluid inlet and the reaction chambers at the periphery of the rotor. A heavy fluid under the influence of centrifugal force is used to push a precise amount of the lighter fluid required for chemical reaction through the passageways to the reaction chambers. The use of a second fluid could cause contamination of the sample.

Neither patents '606 or '602 disclose means within the rotor for separating components of a sample or for mixing a metered quantity of fluid diluent with a sample to be analyzed. Neither do they disclose the use of control cuvettes to provide a check on the accuracy of the system.

U.S. Pat. No. 4,580,898 discloses a rotor having two circumferential rows of chambers, an inner row for samples and an outer row for reagent. The samples are moved by centrifugal force into the reagent chambers to mix the sample and the reagent to form a reaction product which in turn flows into an analysis chamber. The rotor structure has no means for measuring the fluids or for separating a fluid into its components.

PCT/AT 88/00011 to Schaflinger describes a rotor having channels which radiate spirally from the center of the rotor. The rotor must rotate in the direction in which the outer ends of the spiral channels point.

SUMMARY OF THE INVENTION

The object of this invention is to provide a simple analytical apparatus of the kind particularly useful for rapid fluid analysis. Some applications are: analysis of blood, urine, saliva or other body fluids in a doctor's office or clinical laboratory; analysis of environmental samples (soil, water, plant extracts) in the field or laboratory; analysis of animal body fluids in the field or veterinary office.

These analyses include one or more of the following steps: separating a sample into its dense and less dense components; metering a precise amount of sample or one of its components; mixing the sample or one component of the sample with another reagent; dissolving a dry reagent; discharging a sample, a sample component, or sample mixed with reagent to a cuvette for photometric analysis.

Disclosed is an aspect of the invention which allows the performance of each of the steps above rapidly and efficiently, either independently or in one device, by using capillary action and centrifugal force. Once the sample and any reagents are introduced to the rotor, the analysis proceeds by merely adjusting the speed at which the rotor turns. Specifically disclosed is a particular embodiment of the invention which uses all the features in one device to do cholesterol analysis on whole blood.

In one preferred form of the invention, a unique curved separating channel is provided to separate by centrifugal force the less dense components from the more dense components in the sample. The channel has one end spaced radially farther from the center of the rotor than the other end. The configuration of the curved channel preferably is a logarithmic spiral described by the equation:

$$r = ae^{-b\theta}$$

where r is the radius, $\theta$ is the angular position and a and b are constants. The depth of the channel does not affect the rate of settling in percentage terms so the deeper the channel, the more separation of components one can create in a given time. The configuration defined above effects separation more rapidly than a channel on a radius or a straight channel at an angle to a radius. An analysis can consist of evaluating the percentage of total volume each component occupies on the color of one component. One of the components can also be removed for further processing. The dense fraction settles both outward against the channel wall and also outward to the bottom of the channel. Therefore the light fraction is removed from the inner wall and the heavy fraction from the outer wall.

Another aspect of the invention disclosed is a means of metering a precise amount of sample or component of a sample by means of a capillary channel that contains an air vent. This channel fills by capillary action and upon rotating the device, a precise amount of fluid, which is defined by the volume held between the air vent and the outlet, is dispensed.

Another aspect of the invention disclosed is a means for transferring fluid from one chamber to another using only capillary action and centrifugal force. This invention allows one to combine operations in the same device.

The rotor may be molded from plastic material with the chambers and channels or passageways depressed in the surface thereof. The chambers and channels are closed by means of a lid which is secured to the top of the rotor.

In one embodiment that is described in detail to perform cholesterol analysis, the depressions in the molded rotor include a blood chamber and a diluent chamber which are supplied with fluids from an external source through an opening in the lid. The blood chamber connects to a separating channel which in turn connects to a mixing chamber. The diluent chamber also connects to the mixing chamber where diluent and plasma are mixed. The volume of the fluids charged into the mixing chamber is determined by the size of the capillary tubes and/or metering chambers connecting thereto. Overflow chambers are provided to receive the fluid in excess of the capacity of the capillaries or metering chambers. A vented sample cuvette is molded in the rotor near the circumference and connects to the mixing chamber through a siphon mix channel.

In one form of the invention, a vented control cuvette is provided in addition to the sample cuvette. Diluent in excess of the predetermined quantity in the diluent metering chamber is directed to said control cuvette through a series of channels including a siphon capillary channel and a siphon mix channel.

In operation, the diluted plasma or serum reacts with a solid reagent in the sample cuvette to form a color the intensity of which is proportional to the quantity of the blood component being analyzed, for example, cholesterol. The measurement is taken optically. In the form of the invention which includes a control cuvette, the density of the diluent is also optically measured and the value is substracted from the sample reading so that the result reflects only the color from the reaction and not color from the diluent or the material from which the rotor is molded.

In analyzing for cholesterol enzyme, tablets are put into both the sample and control cuvettes. For control purposes, a control tablet containing a known amount of analyte (cholesterol) is also placed in the control cuvette. If the control cuvette does not give a certain predetermined value after the rotor has spun, the machine will reject that rotor. This feature is used to control the integrity of the enzymes as well as the mechanical operation of the machine. Other variations in the use of the control cuvette to check the accuracy of the analyses will be apparent to those skilled in the art.

As the rotor spins initially at the rate of 1,500 revolutions per minute, the serum or plasma is separated from the red cells in the curved separation channel and the diluent which the machine provides, fills the diluent metering chamber. When the rotor stops turning, or when the speed is reduced so that the capillary force is greater than centrifugal force, the serum and diluent fill the capillary channels by capillary attraction. The rotor is spun again at a rate of 300 revolutions per minute for two minutes to dispense plasma and diluent from the capillary channels into the mix chamber. Mixing is accomplished by varying the speed of rotation from 300 to 600 rpm several times. When the rotor stops, the fluids fill the capillaries leading to the cuvettes. The rotor is spun again at the increased rate of 300 to 900 rpm to complete emptying the capillaries into the vented cuvettes. The operation of the device is effective regardless of the direction of rotation. The color in the cuvettes is read with a conventional optical system.

The rotors are economical to produce by molding from a clear plastic such as polymethylmethacrylate, are used for a single analysis and then disposed of.

The capillary channels, which are not vented, are generally V shaped with one leg of the V longer than the other. Under centrifugal force, they empty completely in the direction of the end which is on the longer radius. This principle is used to empty the diluent siphon and siphon mix channels in the rotor.

DESCRIPTION OF THE DRAWINGS

Other objects and advantages will become apparent from the accompanying drawings in which FIG. 1 is a plan view of a rotor constructed in accordance with the invention.

FIG. 2 is a view identical to FIG. 1 and sets forth the location of the cross-sectional views and the air vent openings marked X, which are provided in the lid 24 of the rotor.

FIG. 3 is a sectional view taken along the line 3—3 of FIG. 2.

FIG. 4 is a sectional view taken along the line 4—4 of FIG. 2.

FIG. 5 is a sectional view taken along the line 5—5 of FIG. 2.

FIG. 6 is a sectional view taken along the line 6—6 of FIG. 2.

FIG. 7 is a sectional view taken along the line 7—7 of FIG. 2.

FIG. 8 is a plan view of the lid 24 showing the location of the openings for receiving diluent and sample and for venting various channels and chambers in the rotor.

FIG. 9 is a section taken along the line 9—9 of FIG. 8.

FIGS. 10 through 15, are plan views of the rotor showing fluids being processed at progressive stages of the processing.

DETAILED DESCRIPTION OF A CHOLESTEROL ANALYZER

Figure 12:
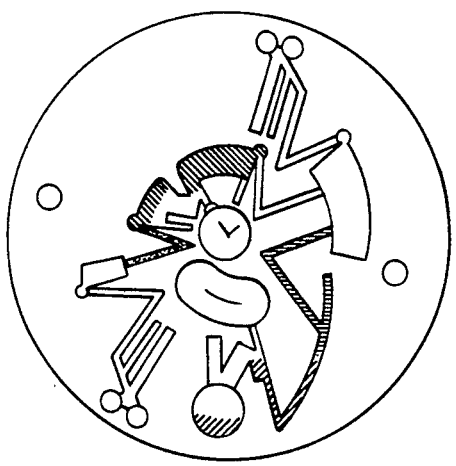

The rotor comprising the novel portion of this invention is indicated generally in FIG. 16 by the numeral 20 and consists of a rotatable element in the form of a plate or disc 22 which has molded in the surface thereof channels and chambers (not shown in FIG. 16) which are interconnected in a manner described below. Plate 22 may have a variety of configurations. The rotor has a cover 24 which encloses the channels and the chambers and is adapted to lock onto the surface of the plate 22. The parts 22, 24 are molded from a transparent plastic such as an acrylic and may be cemented or welded together. The lid 24 contains openings to vent certain of the chambers and passageways as well as to permit charging fluids to be analyzed into the apparatus. Instead of molding the channels and chambers can be machined in a plate-like block of plastic or other material through lateral access, in which case no separate lid is needed.

Figure 16:
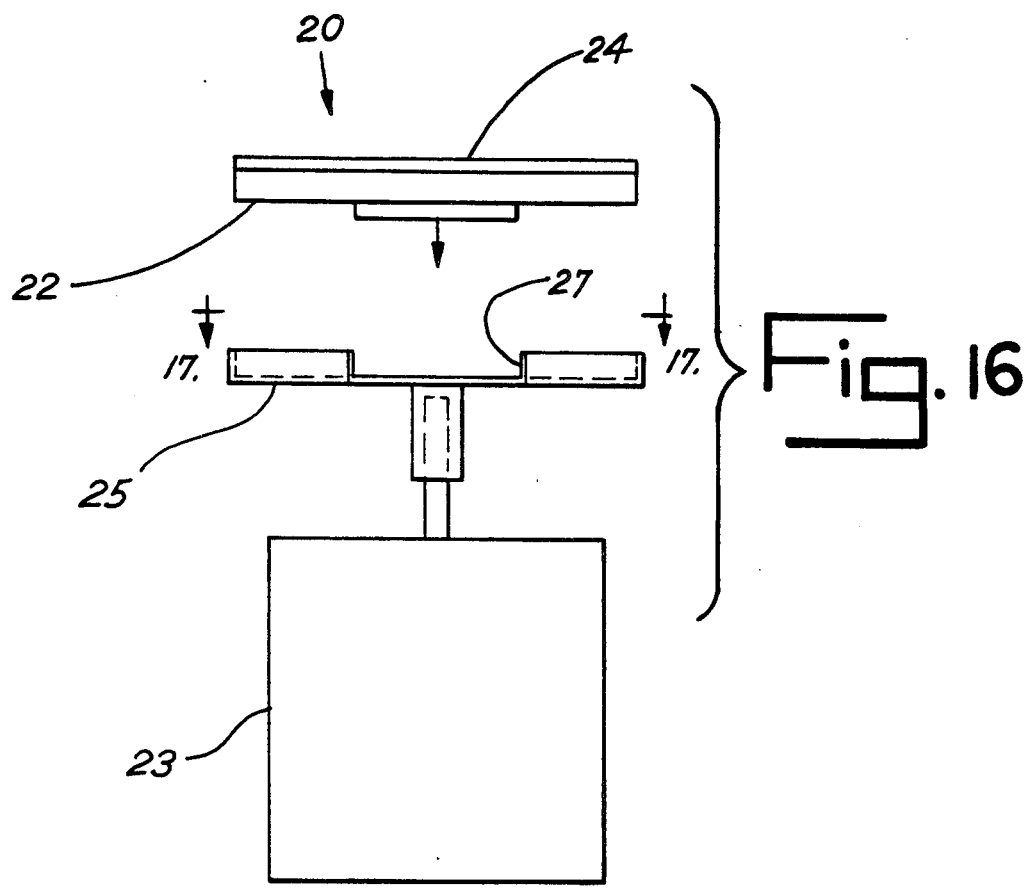
FIG. 16 is an overall view of the apparatus on which the rotor is mounted for rotation.
Figure 17:
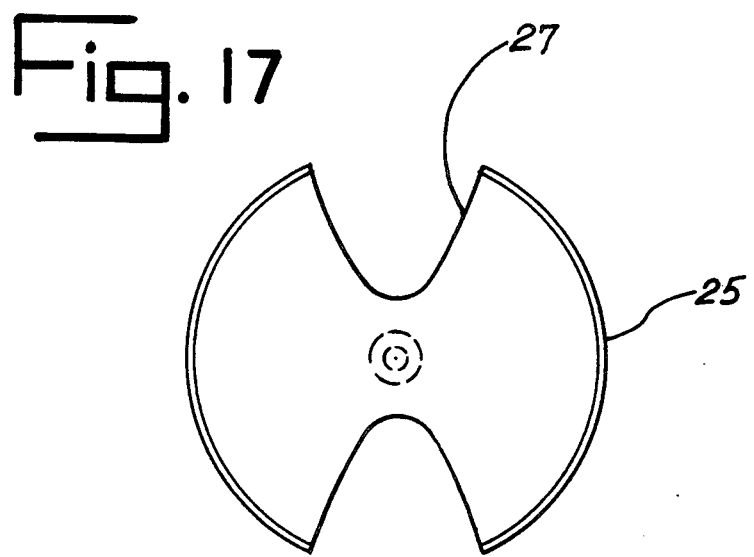
FIG. 17 is a view taken along the line 17—17 of FIG. 16.

As shown in FIG. 16, a base member 25 having opposed surface depressions 27 is mounted on the shaft of a motor 23. The rotor has a pair of bosses on the bottom thereof which fit into the depressions 27 so that the rotor rotates along with the base 25. The bottom portion 22 of the rotor is approximately ¼ inch thick, while the top member 24 is about ⅛ inch thick. Rotatable elements of various configurations may be placed on the single base member to conduct multiple analyses.

The apparatus will now be described in connection with the analysis of a blood sample, but it will be understood that the apparatus is capable of use for other analytical procedures. Referring to FIGS. 1-7, blood chamber 26, molded into the surface of the disc 22 is kidney shaped and its outlet end 28 is disposed radially outward at a point farther from the center of the rotor than the inlet end 30. This facilitates flow of the fluid sample to the outlet end 28. The outer wall 32 of chamber 26 is slanted as indicated in FIG. 3 to allow all of the fluid to flow out of the chamber. The chamber 26 connects to a blood separating channel 36 by means of a connecting channel 34. Channel 34 is enlarged as indicated at 37 so that fluid will fill the separating channel before it flows into the overflow chamber 40 through the overflow channel 38. The overflow channel 38 is wider and deeper than the connecting channel 34 so that capillary action will not fill the overflow channel 38 before the blood separating channel 36 is filled. The amount of blood in excess of that required to fill the separating channel 36 overflows into chamber 40. Chamber 40 communicates through an opening 41 in the lid (FIG. 8) above channel 39 to vent the chamber, thus allowing air to escape as blood enters.

A V-shaped plasma metering channel 42 connects to the separating channel 36 at a point upstream of the end of channel 36. Capillary metering channel 42 is precisely molded to hold a predetermined amount of plasma and is filled by capillary action. Channel 42 also communicates with an air vent in the lid at the point 44 indicated by the letter X in FIG. 2. The predetermined precise amount of plasma is held between the vent 44 in the lid and the outlet 46 of the metering channel. The outlet point 46 must be located on a larger radius from the center of the rotor than is the air vent 44.

A mixing chamber 50 is provided to mix a fluid (plasma) which has been separated from solids (red cells) in the channel 36 with a diluent or other fluid as described below. Chamber 50 has a total volume about twice the volume of the fluid to be mixed so that efficient mixing occurs during acceleration and deceleration of the rotor. The inlet 52 of chamber 50 is located on a larger radius than the other end 54 to allow the mixed fluid to move out of the chamber easily. The walls at the outlet end 52 of chamber 50 are inclined as indicated in FIG. 4 to assist the fluid to move out of the chamber. Chamber 50 communicates through an opening 115 in the lid FIG. 8 which allows air to escape.

A diluent chamber 60 which is accessible through an opening 61 (FIG. 8) in the lid is provided to receive diluent fluid. The chamber 60 is off center toward the outlet side of the chamber to insure that all fluids move out of the chamber during rotation. The wall 62 on the outlet side of chamber 60 is inclined as indicated in FIG. 5 which also facilitates a movement of the fluid out of the chamber. A diluent metering chamber 64 connects to the chamber 60 through the channel 68. Chamber 64 is molded to a predetermined volume. An overflow chamber 66 connects through the channel 70 to chamber 64 and receives any fluid in excess of the amount required to fill chamber 64. The channel 70 is wider and deeper than the channel 68 to prevent capillary action from taking fluid into the overflow chamber before the metering chamber has filled. Both the diluent metering chamber 64 and the overflow chamber 66 are vented through openings 67 and 65 respectively in the lid 24 as shown in FIG. 8. The rounded outlet edges 72 and 74 of chambers 64 and 66 respectively are located at a larger radius than the inlet edges 76 and 78. The outlet corners 72 and 74 of these chambers are inclined as indicated in FIG. 6 to allow the diluent to empty out of the chambers. A capillary diluent siphon channel 84, not vented, connects to mixing chamber 50 at point 86. The point 86 is disposed at a position farther radially outward than the inlet 72 of the diluent siphon channel. V-shaped mix siphon 88 connects to chamber 50 at 52 and is also a capillary channel having an outlet point 90 on a larger radius than the inlet 52. Mix siphon 88 connects at its opposite end and to air vent channel 102 which is of larger cross-section than the mix siphon 88 to allow air bubbles to escape easily out of cuvettes 98, 100 connecting to the outer end thereof. A fluid trap 94 branches from channel 88 and is vented through opening 49 in lid 24. Channel 102 is vented through an opening 104 in the lid 24. A diluent holding chamber 106 connects to the overflow chamber 66 through channel 105. Chamber 106 communicates through an opening 116 in the lid FIG. 8 which allows air to escape. Diluent holding chamber 106 holds the excess diluent through a timing cycle so it does not fill the control cuvettes 108, 110 before the sample cuvettes 98, 100 fill. The cuvettes 108, 110 communicate with chamber 106 through a mix siphon 112. Branching from siphon 112 through channel 96 is an air vent channel 107. Air vent channel 107 is similar to channel 102 and connects to the outer end of mix siphon 112 and to cuvettes 108 and 110. Air vent channel 107 vents through opening 95 in the lid 24.

As best shown in FIG. 9, the sample inlet opening 27 in lid 24 is inclined around its entire circumference to direct the fluid sample into the chamber 26 in the rotor. A vertical walled opening 61 in the lid 24 provides access to the diluent fluid chamber 60.

PRACTICAL OPERATION OF A CHOLESTEROL ANALYZER

The operation of the machine will be explained in a sequence of steps in conjunction with FIGS. 10 through 15 for analysis of blood. These figures repeat the configuration at FIGS. 1 and 2, but numerals have been omitted for the sake of clarity. Enzyme tablets are placed in the cuvettes when the rotor is assembled. To use, 50–200 ul of blood are introduced into the chamber 26 through the opening 27 as shown in FIG. 10. The rotor 20 is placed on the base 17 for rotation by the motor 23. The rotor is accelerated to a speed of 1,500 rpm during which time the blood fills the channel 36 to the radius shown by cross hatching in FIG. 11. Blood in excess of 50 ul goes into the overflow chamber 40. The rotor continues to spin at 1,500 rpm for 2 minutes. The red cells by reason of centrifugal force, are forced to the outer wall of the separation channel 36 while the plasma occupies the space in channel 36 nearest the center of the rotor.

While the rotor is spinning, 350 to 400 ul of diluent are added to the chamber 60 through the opening 61 in the lid. The diluent fills the metering chamber 64 which has a capacity of 250 ul. The remainder of the diluent flows into the diluent overflow chamber 66 as indicated in FIG. 11. The rotor is then brought to a stop or slowed to a point where capillary action is stronger than centrifugal force. By reason of capillary action, plasma fills the plasma metering channel 42 and the diluent fills the diluent siphon channels 84 and 105 as shown in FIG. 12. The rotor speed is then brought up to 300 rpm which causes the diluent siphon channel 84 to begin emptying into the mix chamber 50 and diluent siphon channel 105 to begin emptying into the diluent holding chamber 106. The rotor speed is then increased to 600 rpm to complete emptying the metering chamber 64 and the overflow chamber 66 and to dispense plasma out of metering channel 42, as shown in FIG. 13.

Figure 14:
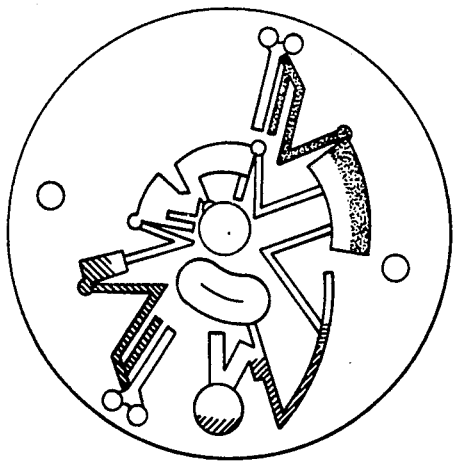
Figure 15:
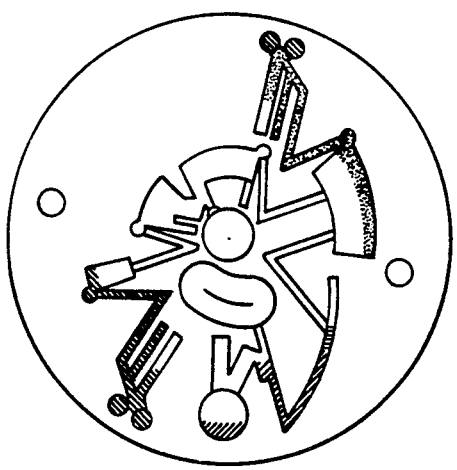

To thoroughly mix the plasma and diluent in the mix chamber 50, the speed of the rotor is changed between 900 rpm and 600 rpm at a high rate of acceleration 4,500 rpm/s several times. The rotor need not be brought to a stop when changing speeds. After the fluids are thoroughly mixed, the rotor is stopped at which time the mix siphon channels 88 and 112 fill by capillary action (FIG. 14). If desired, a stepper motor may be used to vibrate the rotor to enhance the capillary action and fill the channels more quickly. The rotor is again spun at 300–900 rpm which causes channel 88 to empty into the cuvettes 98, 100 and channel 112 to empty into cuvettes 108, 110. (FIG. 15). As the fluid fills the cuvettes, air exits by way of the air vent 104 and 95 (FIG. 2). Enzyme tablets which were placed in the cuvettes at the start of the cycle dissolve when they come in contact with the fluid. The rotor speed may be changed rapidly to accelerate dissolution of the tablet and insure good mixing. After the tablets are dissolved, the optical device (not shown) reads the color in the cuvettes.

The siphon capillary channels 84, 88 are deeper (0.6 mm) than the plasma metering channel 42 (0.3 mm) for two reasons. First, the diluent will empty into the mix chamber 50 before the plasma does and this aids in mixing. Secondly, if the plasma metering channel refills, it will not dispense during subsequent spins because it will take a much higher speed to make the shallower channel dispense compared to the deeper channels.

Figure 13:
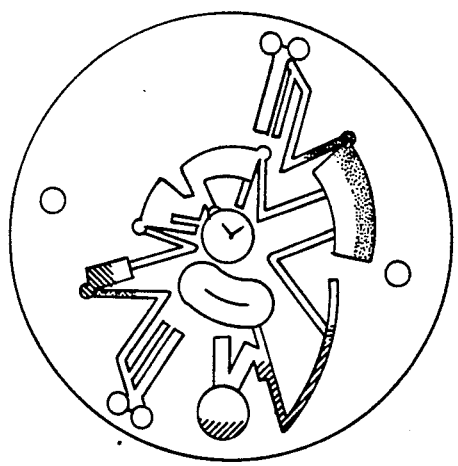

When the diluent and plasma are under centrifugal force in the mix chamber 50, the level of the fluid will be at the point indicated in FIG. 13. A small amount of fluid in the siphon mix channel 88 will not be mixed. This unmixed fluid will enter the fluid trap 94 and not the cuvettes.

After the spin to separate the red cells, the rotor will be brought to a stop slowly which allows the plasma to fill the capillary channel while the cells are still under centrifugal force. This prevents cells from moving into the plasma metering channel. Capillary channels 84, 105, and 112, are not vented and under centrifugal force they empty completely in the direction of the end which is at the longer radius from the center of the rotor. For the length scales typical of this device, gravity is a much weaker force than centrifugal force and surface tension forces. Consequently, devices that depend upon gravity to operate such as sloped floors will not be effective.

DESCRIPTION OF OTHER ANALYZERS

Although the apparatus of the invention has been described above with respect to analyzing blood for cholesterol, it is also suitable for use in other assays. The apparatus may also be used for non-medical analyses which use the rotor principles involved, as for example, for an environmental analysis device. The separating chamber could be used to separate sludge or dirt from a ground water sample. In a "lipid" rotor in which it is necessary to separate high density lipids (HDL), from low density lipids (LDL), whole blood may be metered into a chamber that contains a reagent tablet and diluent added to that chamber. The solution reacts to form a precipitate. This reacted solution is then moved into the separating channel 36 and by spinning the rotor, the precipitate is separated from the fluid. The fluid is then moved to a cuvette containing a tablet of cholesterol enzyme and allowed to react. The color is then read by means of the standard optical device.

Figure 18:
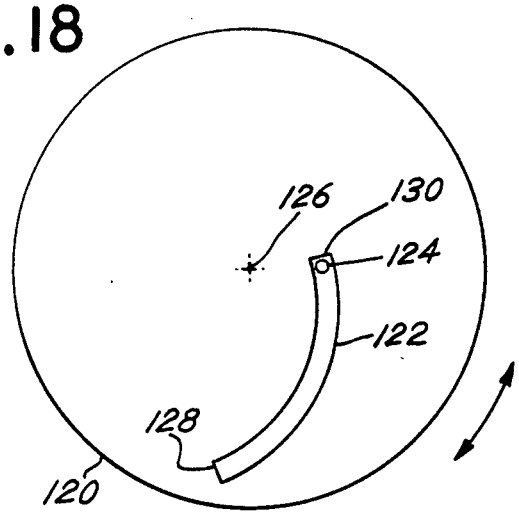
FIG. 18 is a plan view of an analyzing apparatus having a rotor with a single curved channel.

FIG. 18 shows a rotor 120 having a curved channel 122 with an access opening 124 through the cover. The axis of rotation is indicated at 126. This embodiment of the invention is characterized by the fact that the distance from the channel to the axis of rotation becomes progressively shorter in traversing the distance from the outer end 128 to the inner end 130 of the channel 122. This apparatus is suitable for quickly determining the solids fraction of a ground water sample. The channel configuration is a logarithmic spiral defined by the equation set forth above in the summary of the invention.

Figure 19:
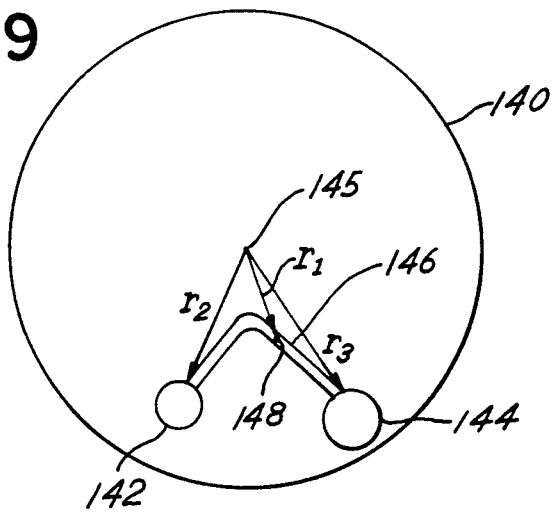
FIG. 19 is a plan view of a rotor having two chambers and an interconnecting vented channel for delivering a precise amount of liquid.

FIG. 19 shows another form of rotor 140 having a first chamber 142 and a second chamber 144 interconnected by channel 146. The channel may be curved rather than V-shaped. The channel is vented at point 148 through the lid which covers the rotor or through the side of the rotor. The vent is closer to the axis of rotation 145 than are the points where the channel connects to chambers 142 and 144 ($r_1 < r_2$; $r_1 < r_3$). The channel 146 is shown in a V-shape but may be curved or straight so long as the distances $r_1$, $r_2$, and $r_3$ are related as indicated with respect to the center of rotation 145. In using this rotor for analysis, a sample to be analyzed is put into chamber 142 and a reagent is placed in chamber 144. A precise volume of the sample, disposed in the capillary channel between vent 148 and chamber 144, is delivered to the reagent in chamber 144 when the rotor is spun.

Figure 20:
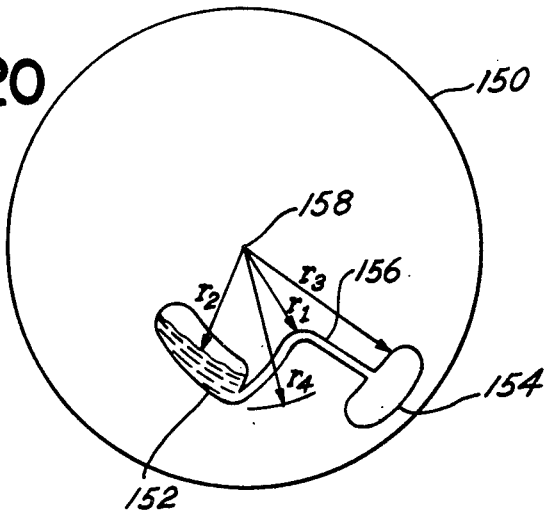
FIG. 20 is a plan view of a rotor in which one of the chambers and the interconnecting channel are precisely located with respect to the axis of rotation.

FIG. 20 shows a modification of the invention in which liquid may be completely transferred from one chamber to another by centrifugal force. The rotor 150 rotates about axis 158. Chamber 152 contains liquid to be transferred to chamber 154 through capillary tube or channel 156. Channel 156 is not vented. Channel 156 connects to chamber 152 at the point where the chamber is farthest from the axis of rotation, spaced a distance $r_4$ from the axis. Channel 156 connects to chamber 154 at a distance $r_3$ from the axis. The maximum level of liquid in chamber 152 is spaced a distance from the axis equal to $r_2$. The channel may be V-shaped, curved, or straight, as long as one point point along the channel, spaced a distance $r_1$, is closer to the axis of rotation than the maximum liquid level and closer than the point where the channel connects to chamber 154, i.e. $r_2 > r_1$; $r_3 > r_1$. The point where the channel connects to chamber 154 is farther from the axis than the point where the channel connects to chamber 152, i.e. $r_3 > r_4$. Liquid in chamber 152 fills channel 156 by capillary action and when the device is rotated, and only when the device is rotated, al the liquid is transferred by centrifugal force through channel 156 to chamber 154. The invention is particularly useful when liquid has been introduced to chamber 152 by centrifugal force and at a later time needs to be transferred to chamber 154.

What is claimed is:

1. In an apparatus for analyzing fluids having components of different density, an improved analyzer rotor comprising:
   a rotatable element mounted for rotation having interconnected chambers and channels disposed in the surface thereof,
   said channels and chambers comprising
   a mixing chamber,
   a diluent capillary channel having one end connecting to said mixing chamber,
   a blood chamber,
   a curved separating channel in communication with said blood chamber for separating red cells from the plasma of whole blood,
   said curved separating channel having one end spaced radially farther from the center of rotation than the opposite end thereof,
   a plasma capillary channel connecting said curved separating channel to said mixing chamber,
   a diluent metering chamber connecting to the other end of said diluent capillary channel, and
   means for rotating said rotatable element at varying speeds to effect movement of fluids through said channels and to mix said separated plasma with diluent.

2. The apparatus of claim 1 in which said channels and chambers also include a sample sample cuvette, an air vent channel connecting to said cuvette and a siphon mix channel interconnecting said sample cuvette with said mixing chamber, said sample cuvette being spaced radially outwardly beyond said mixing chamber.

3. The apparatus of claim 2 which includes a diluent overflow chamber connecting to said diluent metering chamber, a control cuvette, an air vent channel connecting to said control cuvette, a siphon mix channel connecting said control cuvette to said diluent overflow chamber, said control cuvette being spaced radially outwardly from said diluent overflow chamber.

4. The apparatus of claim 3 in which a diluent holding chamber is interposed between said diluent overflow chamber and said siphon mix channel.

5. The apparatus of claim 4 in which said diluent holding chamber connects to said diluent overflow chamber through a diluent siphon capillary channel.

6. The apparatus of claim 1 in which said diluent capillary channel and said plasma capillary channel are generally V-shaped with one leg of the V being longer than the other, said legs extending outwardly toward the circumference of said rotatable element.

7. The apparatus of claim 6 in which said diluent capillary channel is larger in cross section than said plasma capillary channel.

8. The apparatus of claim 6 which includes a diluent overflow chamber connecting to said diluent metering chamber and a blood overflow chamber connecting to said blood chamber through a radial channel.

9. The apparatus of claim 1 which includes a cover over said rotatable element, a first opening through said cover communicating with said blood chamber, a second opening through said cover communicating with diluent metering chamber, and air vent openings communicating with chambers and channels which are vented.

10. The apparatus of claim 9 which includes a circular diluent inlet chamber between said second opening and said diluent metering chamber.

11. The apparatus of claim 10 wherein said inlet chamber has an outlet communicating with said diluent metering chamber and includes a passageway connecting said outlet to said diluent metering chamber and a diluent overflow chamber connecting to said passageway to receive fluid in excess of a predetermined quantity carried by said diluent metering chamber.

12. The apparatus of claim 10 in which said diluent metering chamber and said diluent overflow chamber communicate with air vents to permit filling thereof.

13. The apparatus of claim 1 which includes a vented fluid trap between said siphon mix channel and said sample cuvette.

14. The apparatus of claim 13 in which the inlet of said fluid trap is of smaller cross-section than the inlet to said sample siphon mix channel so that the siphon mix will always empty into said sample cuvette and the liquid in the fluid trap will not empty into said sample cuvette.

15. In an apparatus for analyzing whole blood an improved analyzer rotor comprising
   a rotatable element having interconnected chambers and channels,
   said channels and chambers comprising
   a mixing chamber,
   a diluent capillary channel having one end connecting to said mixing chamber,
   a blood chamber,
   a curved separating channel in communication with said blood chamber for separating red cells from the plasma of whole blood,
   a plasma metering channel connecting said separating channel to said curved mixing chamber,
   a diluent metering chamber connecting to the other end of said diluent capillary channel, and
   means for rotating said rotatable element at varying speeds to effect movement of fluids through said channels and to mix said separated plasma with diluent.

16. The apparatus of claim 15 which includes a vented sample cuvette, a siphon mix channel connecting said sample cuvette to said mixing chamber, a control cuvette and channel means connecting said control cuvette to said diluent metering chamber.

17. The apparatus of claim 16 which includes a cover over said rotatable element, and openings through said cover to provide access to said blood and diluent metering chambers and vents for said cuvettes.

18. The apparatus of claim 16 which includes two or more sample cuvettes and two or more control cuvettes.

19. In an apparatus for separating liquids from solids, gas from liquids or two liquids of different densities an improved analyzer rotor comprising
   a rotatable element mounted for rotation, having interconnecting chambers and channels disposed therein, said channels and chambers comprising
   a sample chamber;
   a curved separating channel having one end spaced radially farther from the center of rotation than the opposite end thereof;
   a connecting channel extending from said sample chamber to said one end of said curved separating channel, and
   means for rotating said rotatable element.

20. The apparatus of claim 19 in which said curved separating channel is curved having a configuration described by the equation $$r = ae^{-b\theta}$$

where r=radius, O is the angular position and a and b are constants.

21. The apparatus of claim 19 which includes a vented cuvette and a channel connecting said vented cuvette to said curved separating channel.

22. In an apparatus comprising a rotatable element mounted for rotation having interconnecting chambers and channels disposed therein and means for rotating said element, an improved fluid metering means comprising
   a fluid chamber
   a capillary channel having an inlet end and an outlet end, said inlet end connecting to said fluid chamber for fluid filling of said capillary channel by capillary action
   a vent on said capillary channel communicating to the atmosphere said capillary channel having a precise predetermined volume between said vent and said outlet end said inlet end and said outlet end being farther from the axis of rotation than said air vent
whereby, upon rotating said element, a precise amount of fluid may be dispensed from the outlet end of said capillary channel by centrifugal force.

23. In an analyzing apparatus comprising a rotatable element mounted for rotation about an axis, said element having interconnecting chambers and channels disposed therein and means for rotating said element, improved means for transferring fluid from one chamber to another comprising
   a first chamber for supplying fluid
   a second chamber for receiving fluid and
   a capillary capillary channel having no vents, the ends of said channel connecting to said first and second chamber respectively, a portion of said capillary channel being closer to the axis of rotation than either said first or said second chambers
   the point where said capillary channel connects to said first chamber being the point of that chamber which is at the greatest distance from said axis, said point also being closer to said axis than the point where the other end of said capillary channel connects it to said second chamber,
whereby upon rotation of said rotatable element fluid is transferred from said first to said second chamber by centrifugal force.

24. An analyzing apparatus comprising a rotatable element having a channel of curved configuration with a first end and a second end, the distance from the channel to the axis of rotation of said rotatable element becoming progressively shorter from said first to said second end, a cover for said channel, an access opening to the channel through said cover and means for rotating said rotatable element.

25. The apparatus of claim 24 in which said channel configuration is defined by the equation $$r = ae^{-b\theta}$$

where r=radius, $\theta$ is the angular position and a and b are constants.

26. In an analyzing apparatus comprising a rotatable element mounted for rotation about an axis, said element having interconnecting chambers and channels disposed therein and means for rotating said element, improved means for transferring fluid from one chamber to another comprising
   a first chamber for supplying fluid
   a second chamber for receiving fluid and
   a capillary channel having no vents, the ends of said channel connecting to said first and second chamber respectively, a portion of said channel being closer to the axis of rotation than either said first or said second chambers
   the point where said capillary channel connects to said first chamber being the point of that chamber which is at the greatest distance from said axis, said point also being closer to said axis than the point where the other end of said capillary channel connects it to said second chamber,
whereby upon rotation of said rotatable element fluid is transferred from said first to said second chamber by centrifugal force.

* * * * *